United States Patent [19]
Dornburg

[11] Patent Number: 6,146,885
[45] Date of Patent: *Nov. 14, 2000

[54] CELL-TYPE SPECIFIC GENE TRANSFER USING RETROVIRAL VECTORS CONTAINING ANTIBODY-ENVELOPE FUSION PROTEINS

[75] Inventor: Ralph C. Dornburg, South River, N.J.

[73] Assignee: University of Medicine and Dentistry of New Jersey, Newark, N.J.

[ * ] Notice: This patent is subject to a terminal disclaimer.

[21] Appl. No.: 08/279,307

[22] Filed: Jul. 22, 1994

Related U.S. Application Data

[63] Continuation of application No. 07/979,619, Nov. 20, 1992, abandoned.

[51] Int. Cl.[7] .................................................... C12N 15/86
[52] U.S. Cl. .................. 435/320.1; 536/23.4; 536/23.53; 536/23.72
[58] Field of Search ................................. 435/69.1, 69.7, 435/172.1, 320.1; 935/22, 23, 32, 57; 536/23.1, 23.4, 23.53, 23.72

[56] References Cited

FOREIGN PATENT DOCUMENTS

| | | |
|---|---|---|
| WO 90 12087 | 10/1990 | WIPO . |
| WO 92 06180 | 4/1992 | WIPO . |
| WO 93 00103 | 1/1993 | WIPO . |
| WO 94 06920 | 3/1994 | WIPO . |
| WO 94 12626 | 6/1994 | WIPO . |

OTHER PUBLICATIONS

Orpin et al., "Report and Recommendations of the Panel to Assess the NIH Investment in Research on Gene Therapy", Dec. 7, 1995.
Verma et al., Nature, vol. 389, pp. 239–242, Sep. 18, 1997.
Eliot Marshall, "Gene Therapy's Growing Pains", Science, vol. 269, Aug. 25, 1995, pp. 1050–1055.
Russell et al., "Retroviral Vectors Displaying Functional Antibody, Fragments", Nucleic Acids Res., vol. 21, No. 5, 1993, pp. 1081–1085.
Kewalramani, V.N., et al. "Spleen Necrosis Virus, an avian innunossupressive retrovirus, shares a receptor with the type D simian retroviruses", *Journal of Virology*, vol. 66, No. 5, May 1992, pp. 3026–3031.
Riley, S.C., et al. "Preferential expression of variable region heavy chain gene segments by predominant 2,4–dinitrophenyl–specific BALB/c neonatal antibody clonotypes," *Proceedings of the National Academy of Sciences of USA*, vol. 83, No. 8, Apr. 1986, pp. 2589–2593.
Te–Hua, T.C., et al. "Cell targeting with retroviral vector particles containing antibody–envelope fusion proteins," *Gene Therapy*, vol. 1, No. 5, Sep. 1994, pp. 292–299.

*Primary Examiner*—David Guzo
*Attorney, Agent, or Firm*—McDonnell, Boehnen, Hulbert & Berghoff

[57] ABSTRACT

The present invention pertains to retroviral vector particles having target cell specificity which comprise a retroviral vector having an antigen binding site of an antibody fused to the envelope protein of the retroviral vector, wherein the antigen binding site of the antibody replaces the natural viral receptor binding site.

2 Claims, 3 Drawing Sheets pSNV-env-mC pSNV-env-mD pTC4 pTC5 pJD214 HV

FIG. 3

| | | | |
|---|---|---|---|
| ACTGGAGGCT | GATTTTTGAA | GAAAGGGGTT | GTAGCCTAAA | AGATGATGT |
| GTTAAGTCTT | CTGTACCTGT | TGACAGCCCT | TCCGGGTATC | CTGTCAGAGG |
| TGCAGCTTCA | GGAGTCAGGA | CCTAGCCCTG | TGAAACCTTC | TCTGACTCTG |
| TCCCTCACCT | GTTCTGTCAC | TGGCGACTCC | ATCACCAGTG | GTTACTGGAA |
| CTGGATCCGG | AAATTCCCAG | GGAATAAAACT | TGAGTACATG | GGGTACATAA |
| GCTACAGTGG | TAGCACTTAC | TACAATCCAT | CTCTCAAAAG | TCGAATCTCC |
| ATCACTCGAG | ACACATCCAA | GAACCAGTAC | TACCTGCAGT | TGAATTCTGT |
| GACTACTGAG | GACACAGCCA | CATATTACTG | TGCAAGATAT | GGTGGTAACT |
| ATGCTATGGA | GTACTGGGGT | CAAGGAACCT | CAGTCACCGT | CTCCTCAGGA |
| GGTGGCGGTA | CAGGTGGCGG | AGGTACAGGC | GGAGGTGGTA | GAATTGTGAT |
| GACACAGTCT | CCATCCTCCC | TGGCTATGTC | AGTAGGACAG | AAGGTCACTA |
| TGAGCTGCAA | GTCCAGTCAG | AGCCTTTTAA | ATAGTAGCAA | TCAAAAGAAC |
| TATTTGGCCT | GGTACCAGCA | GAAACCAGGA | CAGTCTCCTA | AACTTCTGT |
| ATACTTTGCA | TCCACTAGGG | AATCTGGGGT | CCCTGATCGC | TTCATAGGCA |
| GTGGATCTGG | GACAGATTTC | ACTCTTACCA | TCAGCAGTGT | GCAGGCTGAA |
| GACCTGGCAG | ATTACTTCTG | TCAGCAACAT | TATAGCACTC | CGTGGACGTT |
| CGGTGGAGGC | ACCAAGCTGG | AAATCAAACG | GGCTGA | |

CELL-TYPE SPECIFIC GENE TRANSFER USING RETROVIRAL VECTORS CONTAINING ANTIBODY-ENVELOPE FUSION PROTEINS

CROSS REFERENCE

This is a continuation of U.S. Ser. No. 07,979,619, filed Nov. 20, 1992 (now abandoned).

BACKGROUND OF THE INVENTION

1. Field of the Invention

This invention relates to retroviral vector particles having target cell specificity. The retroviral vector particles comprise a retroviral vector having an antigen binding site of an antibody fused to the envelope protein of the retroviral vector. The antigen binding site of the antibody replaces the natural viral receptor binding site. This invention also relates to a method for preparing the retroviral vector particles and a method for using the retroviral vectors to introduce genes into vertebrate cells.

2. Description of the Background

The disclosures referred to herein to illustrate the background of the invention and to provide additional detail with respect to its practice are incorporated herein by reference. For convenience, the disclosures are referenced in the following text and respectively grouped in the appended bibliography.

Retroviral vectors are the most efficient tools to introduce genes into vertebrate cells. Clinical experiments have been conducted to use retrovirus vectors to cure a genetic disease in humans (adenosine deaminase (ADA) deficiency). Besides correcting inborn errors of metabolism, gene therapy is also being tested in clinical trials to cure cancer and various other diseases (Science 1992, Vol. 258, pp. 744–746).

Retroviral vectors are basically retroviral particles that contain a genome in which all viral protein coding sequences have been replaced with the gene(s) of interest. As a result, such viruses cannot further replicate after one round of infection. Retroviral vector particles are produced by helper cells (FIG. 1). Such helper cells are cell lines that contain plasmid constructs which express all retroviral proteins necessary for replication. After transfection of the vector genome into such helper cells, the vector genome is encapsidated into virus particles (due the presence of specific encapsidation sequences). Virus particles are released from the helper cell carrying a genome containing only the gene(s) of interest (FIG. 1). In the last decade, several retroviral vector systems, derived from chicken or murine retroviruses, have been developed for the expression of various genes (for reviews see Temin, 1987; Gilboa, 1990).

Retroviral vectors have several limitations. Besides the limited genome size that can be encapsidated into viral particles, the most limiting factor for the application of retroviral vectors is the restricted host range of the vector particle. Some retroviruses can only infect cells of one species (ecotropic retroviruses) or even only one cell-type of one species (e.g., HIV). Other retroviruses have a very broad host range and can infect many different types of tissues of many different species (amphotropic retroviruses).

The initial step of retroviral infection is the binding of the viral envelope (env) glycoprotein to specific cell membrane receptors, the nature of which is unknown for most retroviruses. However, the interaction of the viral env protein with the cell surface receptor is very specific and determines cell-type specificity of a particular virus (Weiss et al, 1985). The envelope protein of all known retroviruses is made up of two associated peptides, (e.g., gp70and p20(E) in SNV). These peptides are derived by proteolytic cleavage from the same precursor (gPR90env) encoded by the retroviral env gene. One peptide p20(E), also termed TM, anchors the protein in the membrane of the virus and, as shown with HIV, mediates the fusion of the virus and cell membranes. The second peptide gp70, also termed SU, mediates the binding of the virus to its receptor and, therefore, determines the host range (Weiss et al., 1985; Varmus and Brown, 1989).

BRIEF DESCRIPTION OF THE FIGURES

FIG. 3 shows the sequence of the single chain antibody gene (scFv) against the hapten DNP (SEQ ID NO:1).

SUMMARY OF THE INVENTION

Figure 1A:
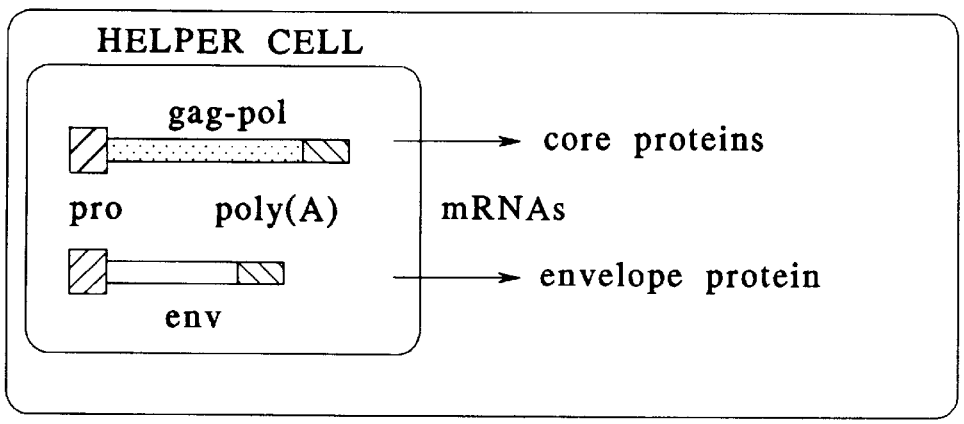
FIG. 1 is a diagram illustrating helper cells expressing retroviral proteins. A) Helper cells are made by the transfection of plasmids expressing all retroviral proteins necessary to form infectious virus particles. B) After transfection of the retroviral vector, the vector RNA genome is encapsidated into core structures. C) Helper cells that contain a plasmid express a modified envelope gene.

In one embodiment, the present invention pertains to a retroviral vector particle having target cell specificity which comprises a retroviral vector having an antigen binding site of an antibody fused to the envelope protein of the retroviral vector, wherein the antigen binding site of the antibody replaces the natural viral receptor binding site.

In another embodiment, the present invention pertains to a cell type specific method for introducing genes into vertebrate cells using retroviral vectors which comprises administering to the cells a retroviral vector particle having target cell specificity which comprises a retroviral vector having an antigen binding site of an antibody fused to the envelope protein of the retroviral vector, wherein the antigen binding site of the antibody replaces the natural viral receptor binding site.

In yet another embodiment, the present invention pertains to a method for preparing a retroviral vector particle having target cell specificity which comprises a retroviral vector having an antigen binding site of an antibody fused to the envelope protein of the retroviral vector, wherein the antigen binding site of the antibody replaces the natural viral receptor binding site, which comprises the steps of:

(a) providing a single chain antibody gene;

(b) replacing part of the envelope gene coding for the viral receptor binding site with the antibody gene to form a chimeric envelope gene;

(c) cloning the chimeric envelope gene in a eucaryotic gene expression vector; and (d) cotransfecting the chimeric envelope expression plasmid, a retroviral core protein expression plasmid, and a selectable marker gene expression plasmids into eucaryotic cells.

DETAILED DESCRIPTION OF THE INVENTION

This invention relates to retroviral vector particles having target cell specificity. The retroviral vector particles comprise a retroviral vector having an antigen binding site of an antibody fused to the envelope protein of the retroviral vector. The antigen binding site of the antibody replaces the natural viral receptor binding site. This invention also relates to a method for preparing the retroviral vector particles and a method for using the retroviral vectors to introduce genes into vertebrate cells.

To alter the host range of a vector particle, retroviral vector particles may be constructed that contain modified envelope proteins that recognize only a cell surface structure (receptor) specific for the target cell of interest. Proteins known to recognize specific structures of proteins are antibody molecules. Hence, to make a retroviral vector particle specific for a cell-type of interest, the viral receptor binding peptide may be replaced with an antigen binding site of an antibody molecule. To test whether vector particles containing such antigen binding sites are competent for infection, model systems were developed using an antigen binding peptide of an antibody against the hapten dinitrophenol (DNP) fused to envelope gene of spleen necrosis virus (SNV).

The use of the anti-hapten (anti-DNP) antibody has many advantages. (1) The interaction of this antigen with the antibody is well characterized (Davies and Metzger, 1983). (2) The hapten is easily available. (3) A large variety of cells (which cannot be infected with wild-type vector particles) can be conjugated with this hapten. DNP conjugated cells bind antibodies directed against this hapten. Thus, the hapten may mimic the (abundant) presence of a receptor for the chimeric vector particle. (4) Anti-hapten antibodies are frequently internalized by the cell. Thus, in the case, the construction of chimeric envelope proteins will destroy the membrane fusion domain of TM, this property may compensate for this loss of function. (5) An in vitro binding assay can be easily established to test for virus particle formation and binding of such viruses to DNP.

EXAMPLES

Materials and Methods

Construction of Antibody-Envelope Fusion Genes

The gene coding for the envelope protein of spleen necrosis virus (SNV) does not contain suitable restriction enzyme sites to enable the construction of antibody-envelope fusion genes. Thus, point mutations were introduced (by site directed mutagenesis) in the SNV env gene at different locations to create restriction enzyme recognition sites. For this purpose, the SNV env gene (HindIII-SacI fragment) was subcloned into pSelect (a vector specifically designed for site directed mutagenesis). Restriction sites for enzymes that create blunt ends were introduced in such a way that the restriction enzymes cut between two codons. Following consistently this strategy, all mutants can be used to create deletions, insertions, and fusions in any combination without altering the reading frame. Further, restriction enzyme sites were nested between regions coding for hydrophobic and hydrophilic domains. It was hypothesized that the deletion of a certain domain(s) would not interfere with the proper folding of the following domain. This hypothesis is based on the finding that many proteins in evolution arose by exon shuffling of functional domains.

Some mutant envelopes that have been made are shown in FIG. 2. pSNV-env-mC (FIG. 2a) contains a new restriction enzyme site located between a hydrophobic and a hydrophilic peptide domain. In this mutant, the change in the nucleotide sequence does not alter the amino acid sequence. Thus, pSNV-env-mC can be considered as a positive control. pSNV-env-mD contains a new restriction enzyme site within the cleavage site of the envelope precursor. The introduction of the mutation also altered the amino acid sequence destroying the common motive found in all cleavage sites of all retroviruses investigated. Thus, it was expected that the resulting envelope precursor would not be cleaved, and, therefore, would not to give rise to infectious virus particles. Mutated env genes were inserted into pHB3, a eucaryotic gene expression vector (FIG. 2).

Figure 2A:
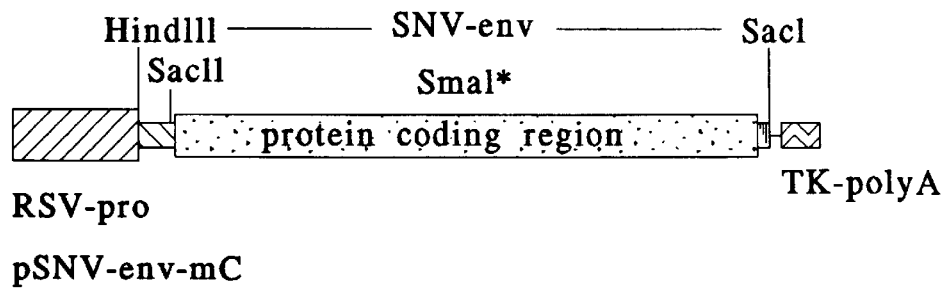
FIG. 2 is a diagram illustrating plasmids expressing mutant envelope genes of spleen necrosis virus (SNV).
Figure 2B:
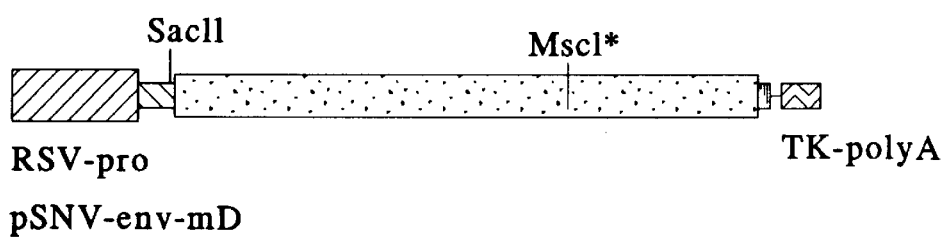
Figure 2C:
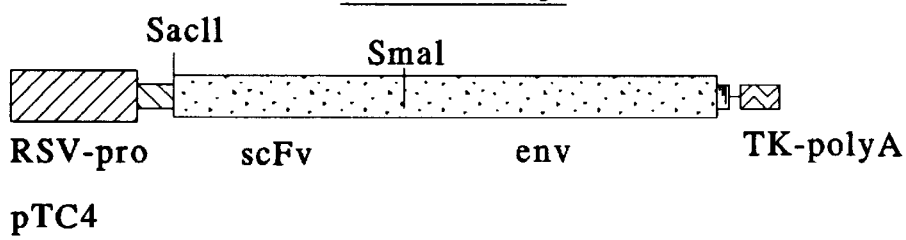
Figure 2D:
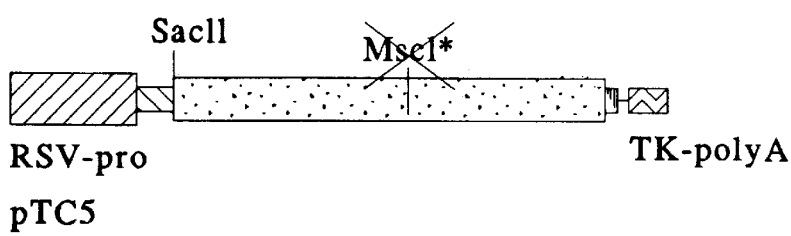
Figure 2E:
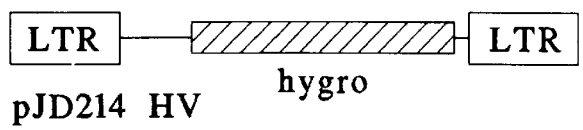

The genes coding for the heavy and the light chain of an antibody against DNP have been kindly provided by Dr. Ogawa (Scripps Clinic, La Jolla, Calif.). The genes were sequenced and published (Riley et al., 1986). Using PCR technology as described (Whitlow and Filpula, 1990), a single chain antibody gene was constructed including the signal peptide against DNP. The PCR product was cloned into the SmaI site of pBluescript. DNA sequencing confirmed the successful combination of the two gene segments coding for the variable regions of the antigen binding peptide. The complete sequence of the anti-DNP scFv gene is given in FIG. 3. A SacII (located in the polylinker of pBluescript) to SmaI (located in the 3' PCR primer) fragment was inserted into eucaryotic expression vectors replacing amino terminal parts of the envelope gene as follows: in pTC4, the SacII (located upstream of the ATG codon of the env gene) to SmaI fragment of env was replaced with the scFv gene; in pTC5 the SacII to the MscI fragment of env was replaced with the scFv gene (FIGS. 2C and 2D, respectively). After cloning, the antibody-envelope junctions were sequenced to verify the maintenance of the correct reading frame of the chimeric gene.

In vitro Binding Assays

The in vitro binding assays were performed in the following manner. DNP was conjugated to BSA (DNP-BSA was used to raise the initial antibodies from which the scFv genes have been derived). DNP-BSA was coupled to activated Sepharose following the protocol recommended by the supplier (Sigma). An Elisa assay with a anti-DNP antibody (kindly provided by Dr. S. Pestka) confirmed the successful coupling reaction. 100 ml of tissue culture supernatant medium was incubated with 50 ml of DNP-BSA-Sepharose for 30 minutes at 37° C. After incubation, the sepharose particles were pelleted by centrifugation in a Qualitron minicentrifuge for 30 seconds. The pellets were rinsed once with PBS. The PBS was removed and reverse transcription assays were performed by adding the reaction to the sepharose pellet. The reverse transcription assay was done using standard procedures; incorporation of 32PdTTP into cDNA was determined by TCA precipitation as described (Schleif and Wensink, 1981).

Test for Infectivity of Particles Containing Antibody-Envelope Fusion Proteins

Figure 1B:
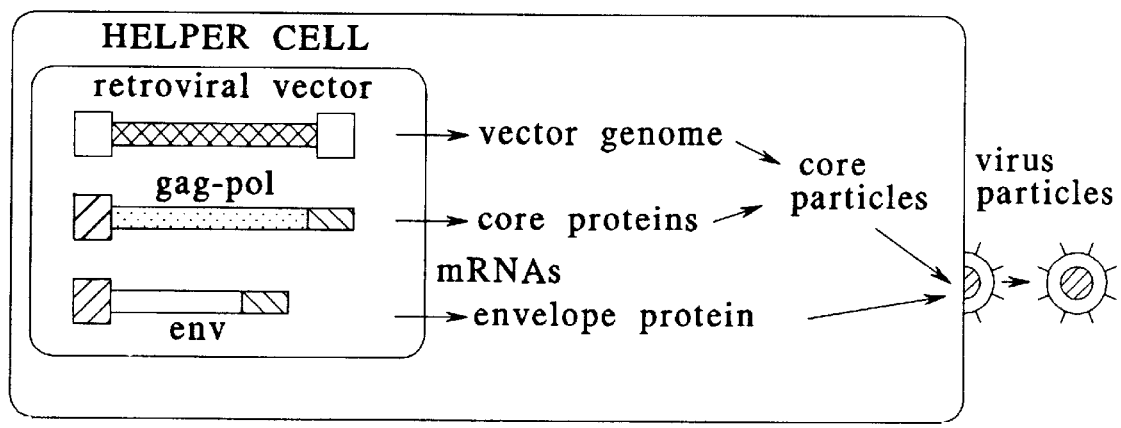
Figure 1C:
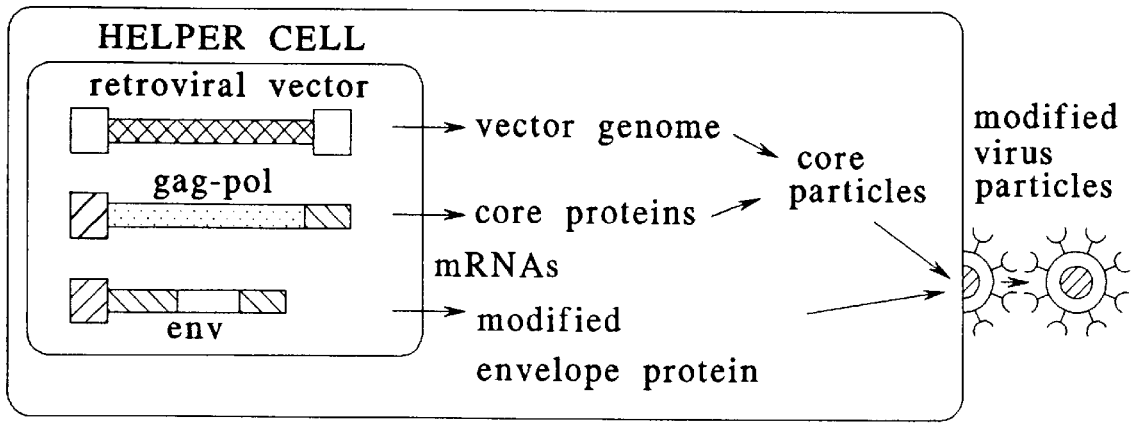

The envelope expression plasmids shown in FIG. 2 were transfected into D17 cells (a dog osteosarcoma cell-line) in cotransfection with pBR1 and pJD214HY (FIG. 2), plasmids expressing the retroviral core proteins, and containing a retroviral vector for the expression of the hygromycin phosphotransferase gene, respectively (see also FIG. 1). Cells were selected for hygromycin resistance. After selection for hygromycin resistance, virus was harvested from confluent cell cultures and infectivity assays were performed (see below). Infected target cells were selected for hygromycin resistance (D17 cells were incubated with medium containing 60 mg/ml hygromycin, CHO cells with medium containing 250 mg/ml hygromycin). Hygromycin resistant cell colonies indicate infectious virus particles.

Infectivity assays were performed on D17 and CHO cells with and without conjugated DNP. DNP was conjugated to cells as follows: Cells were incubated with 500 ml of a solution containing 1.4 mg/ml DNBS (2,4,-Dinitrobenzene-sulfonic acid, 2-hydrate, purchased from Kodak) in sodium cocodylate buffer (0.25M) for 3 to 5 minutes at room temperature. The conjugation reaction was stopped by adding 5 ml of medium to the cells.

Infections of non-conjugated cells were performed in the presence of 50 mM polybrene using standard protocols. In the case of DNP conjugated cells, infection was performed without polybrene.

Results

In vitro binding assay. The in vitro binding assays showed that only 30 cells transfected with pSNV-env-mD produce viral vector particles that contain a chimeric envelope able to bind DNP (see also Table 1).

Infectivity studies. The results of the infectivity experiments are summarized in Table 1. Vector particles containing wild-type envelope (pSNV-env-mC) infected D17 cells with an efficiency of about 105 colony forming units per ml of tissue culture supernatant medium. Such virus particles also infected D17 cells conjugated with DNP. However, the efficiency of infection was three orders of magnitude less than that of cells not conjugated with DNP. This drop in virus titer is mainly due to difficulties of selecting DNP conjugated cells with the antibiotic. It appears that the conjugation reaction makes cells very vulnerable to the drug and more than 90% of the cells died two to three days after the conjugation reaction. Virus particles with wild-type envelope do not infect CHO cells.

The mutation of the cleavage site of the envelope precursor protein (SNV-env-mD) completely abolished infectivity. Only one colony was observed in D17 cells not conjugated with DNP. This finding coincides with earlier reports that mutations in the envelope precursor cleavage site lead to non-infectious virus particles. Cells transfected with pTC4 (FIG. 2) did not produce vector particles that were able to infect D17 or CHO cells at significant efficiencies. Cells transfected with pTC5 produced virus particles unable to infect D17 or CHO cells. However, such particles significantly infected cells conjugated with DNP.

Discussion

The data obtained with retroviral particles containing antibody-envelope fusion proteins showed that such particles are competent for infection. Surprisingly, TC4, a construct that contains the scFv gene fused to env in the middle of SU did not give virus particles capable of binding DNP. This may be due to an unstable SU-TM complex. This hypothesis is supported by the finding that such particles failed to bind to DNP-BSA-Sepharose. Low level infectivity of such particles on D17 cells may result from unspecific adsorption of virus particles containing TM only. Unspecifically adsorbed virus particles (depleted of SU) may occasional penetrate the cell.

Cells transfected with pTC5 produce virus particles with chimeric envelopes without a functional retroviral membrane fusion domain. This assumption is based on the finding that virus particles containing uncleaved envelope precursor proteins (SNV-env-mD) are not infectious. However, it is known that some antibody molecules are internalized by cells after binding to cell surface by an unknown mechanism. The data show that such an internalization mechanism might be sufficient to allow internalization of the virus particle and the consequent establishment of a successful infection.

Applications of Vector Particles With Antibody-Envelope Fusion Proteins in Gene Therapy In all applications of human gene therapy so far, the cells of interest were isolated from the patient, purified from other cell types, and infected in tissue culture with retroviral vector particles which were harvested from helper cells. After expansion of the treated cells in tissue culture, they were re-injected into the patient. The infection of cells has to be done in vitro, since the retroviral vector particles used (derived from amphotropic murine retroviruses) have a broad host range. Thus, if injected directly into the blood stream of a patient, such virus particles would infect all kinds of tissue. Besides other risks, this treatment would be inefficient, since the chance that the gene will be delivered to its appropriate target cell is very low.

This clinical gene therapy protocol may be sufficient to obtain insight into how efficient and how beneficiary gene therapy will be for the patient. Indeed, the clinical data look very promising (Eglitis, personal communication). However, the current clinical protocol is very laborious, time consuming, very costly, and, therefore, not suitable for general clinical application. For general clinical application, it will be necessary to inject the gene transfer vehicle directly into the body of the patient.

The development of a retroviral vector particle that only infects one specific cell type, may allow the direct injection of the vector into the patient's blood stream. The development of vector particles containing antibody-envelope chimeras may be the first step towards this goal and may open a new area of possible applications of gene therapy in vivo.

TABLE 1

Infectivity of Retroviral Vector Particles on D17 and CHO Cells With and Without DNP Conjugation*

| Envelope of virus particle | Virus titer (cfu/ml) Binding to DNP | D17 cells | D17 + DNP | CHO − DNP | CHO + DNP |
|---|---|---|---|---|---|
| SNV-env-mC | nd | $10^5$ | $10^2$ | 0 | 0 |
| SNV-env-mD | − | 1 | 0 | 0 | 0 |
| TC4 | − | 10 | 0 | 0 | 1 |
| TC5 | + | 0 | $10^2$ | 0 | 10 |

*Virus was harvested from tissue culture cells expressing SNV gag-pol and the envelope protein indicated in the left column (see also FIG. 2). All cells contained pJD214HY, a retroviral vector expressing the hygromycin B phosphotransferase gene. Infected cells were selected for hygromycin resistance. The number of hygromycin resistant cell colonies was determined two to three weeks after infection (after all cells had died in uninfected control plates). DNP binding of vector particles was the determined by measuring reverse transcriptase activity bound to DNP-BSA-Sepharose particles. nd: not determined; 0: no hygromycin resistant colonies were detected. Virus titers are expressed as colony forming units (cfu) per ml of tissue culture supernatant medium.

The term "oligonucleotide" as used herein refers to primers, probes, oligomer fragments to be detected, oligomer controls, and unlabeled blocking oligomers. Oligonucleotide are molecules comprised of two or more deoxyribonucleotides or ribonucleotides. The term "primer" as used herein refers to an oligonucleotide, preferably an oligodeoxyribonucleotide, either naturally occurring such as a purified restriction digest or synthetically produced, which is capable of acting as a point of initiation of synthesis when subjected to conditions in which synthesis of a primer extension product, which is complementary to a nucleic acid strand, is induced, i.e., in the presence of nucleotides, an agent for polymerization such as a DNA polymerase, and a suitable temperature and pH. The primer must be sufficiently long to prime the synthesis of extension products in the presence of the polymerization agent. Methods for amplifying and detecting nucleic acid sequences by polymerase chain reaction (PCR) are described in detail in U.S. Pat. Nos. 4,683,195, 4,683,202, and 4,965,188, which disclosures are incorporated herein by reference.

FIG. 1 is a diagram illustrating helper cells expressing retroviral proteins. A) Helper cells are made by the transfection of plasmids expressing all retroviral proteins necessary to form infectious virus particles. One plasmid is designed to express all core/proteins (expression of gag and pol). The other plasmid is designed to express the envelope precursor/protein. Both plasmid constructs do not contain retroviral cis/acting sequences for virus replication (e.g., encapsidation sequences, a primer binding site etc.). Polyadenylation takes place in non/retroviral polyadenylation recognition sequences. B) After transfection of the retroviral vector, the vector RNA genome is encapsidated into core structures. The helper cell is producing retroviral particles that only contain the vector genome with the gene(s) of interest. The vector contains all cis/acting sequences for replication. Thus, in infected target cells, the vector genome is reverse transcribed and integrated into the genome. Due to the lack of retroviral protein coding genes in the vector genome, no virus particles are produced from infected target cells. C) Helper cells that contain a plasmid express a modified envelope gene. The helper cell is very similar to that shown above. However, chimeric envelope genes were constructed that contain the antigen binding domain of an antibody at the amino terminus fused to the carboxy terminus of the envelope gene. Such particles may only bind to and infect target cells that contain an antigen structure which is recognized by the antibody moiety of the chimeric envelope protein.

FIG. 2 is a diagram illustrating plasmids expressing mutant envelope genes of spleen necrosis virus (SNV). Genes are expressed from the Rous sarcoma virus promoter (RSV/pro) and polyadenylated within the polyadenylation signal of herpes simplex virus thymidine kinase gene (TK/poly(A)). The polylinker of pBluescript was inserted between the promoter and the polyadenylation sequence to allow the easy cloning of genes into this vector (plasmid sequences that abut the vector are not shown). a/b) point mutations were introduced into the env gene by site directed mutagenesis to create new restriction enzyme recognition sites (indicated by an *). All enzymes cut exactly between two codons creating blunt ends for easy ligation without shifting the reading frame. c/d) chimeric envelope of containing an antigen binding peptide fused to the carboxy terminus of env. e) pJD214Hy, a retroviral vector used in all studies to test the transfer of genes by retroviral vector particles.

FIG. 3 shows the sequence of the single chain antibody gene (scFv) against the hapten DNP (SEQ ID NO:1).

Appendium of References

Bird, R. E., Hardman, K. D., Jacobson, J. W., Johnson, S., Kaufman, B. M., Lee, S. -M., Lee, T., Pope, S. H., Riordan, G. S., and Whitlow. M. 1988. Single-chain antigen binding proteins. Science, 242:423–426.

Colcher, D., Bird, R., Roselli, M., Hardman, K. D., Johnson, S., Pope, S., Dodd, S. W., Pantoliano, M. W., Milenic, D. E., Schlom, J. 1990. In vitro tumor targeting of a recombinant single-chain antigen-binding protein, J. Natl. Canc. Inst. 82:1191–1197.

Cone, R. D. and Mulligan, R. C. 1984. High-efficiency gene transfer into mammalian cells: generation of helper-free recombinant retroyirus with broad mammalian host range. Proc. Natl. Acad. Sci. USA 81:6349–6353.

Cournoyer, D., Scarpa, M., Jones, S. N., Moore, K. A., Belmont, J. W., and Caskey, C. T. 1990. Gene therapy: a new approach for the treatment of genetic disorders, Clin. Pharmacol. Ther. 47(1):1–11.

Danos, O. and Mulligen, R. C. 1988. Safe and efficient generation of recombinant retroviruses with amphotropic and ecotropic host ranges. Proo, Natl. Acad. Sci. 85:6460–6464.

Davies, M. M. and Metzger, H. 1983. Structural basis of antibody function. Annu. Rev. Immunol. 1:87–117.

Friedmann, T. 1989. Progress toward human gene therapy. Science 244, 1275–1281.

Gritz, L., and J. Davies. 1983. Plasmid encoded hygromycin B resistance: the sequence of hygromycin B phosphotransferase gene and its expression in Escherichia coli and Saccharomyces cerevisiae. Gene 25, 179–188.

Hunter, E. and Swanstrom. R. 1990. Retrovirus envelope glycoproteins. Curr, Top. Microbiol. Immunol. 157:187–253.

Kohn, D. B., Anderson, W. F., and Blaese, M. B. 1989. Gene therapy for genetic diseases. Cancer Investigation 7(2):179–192.

Larson, S. M. 1990. Improved tumor targeting with radiolabeled, recombinant, single-chain, antigen-binding protein. J. Natl. Canc. Inst. 82 1189–1190.

Markowitz, D., Goff, S., and Bank, A. 1988, A safe packaging line for gene transfer: separation of viral genes on two different plasmids. J. Virol. 62:1120–1124.

Miller, A. D, 1990. Progress toward human gene therapy. Blood 76(2):271–278.

Mims, C. A. 1986. Virus receptors and cell tropism. J. Infect. 12:199–204. Riley, S. C., Connors, S. J., Klinman, N. R., and Ogata, R. T. 1986. Preferential expression of variable region heavy chain gene segments by predominant 2,4-dinitrophenyl-specific BALB/c neonatal antibody clonotypes. Proc. Natl. Acad. Sci. 83:2589–2593.

Rolt, I. 1988. In "Essential Immunology". Blackwell Scientific Publications.

Temin, H. M. 1986. Retrovirus vectors for gene transfer: efficient integration into and expression of exogenous DNA in vertebrate cell genomes, in "Gene Transfer" (R. Kucherlapati, ed.) Plenum Press, N.Y.

Varmus, H. E., and Brown, P. 1988. Retroviruses, in "Mobile DNA" (M. Howe and D. Berg, eds.) ASM, Washington D.C., Watanobe, S., and H. M. Temin. 1983. Construction of a helper cell line for avian reticuloendotheliosts virus cloning vectors. Mol. Cell. Biol. 3, 2241–2249.

Weiss, R., Telch, N., Vermus, H., and Coffin, J. 1985. RNA tumor viruses. Cold spring harbor Laboratory, Cold Spring Harbor, N.Y.

Whitlow, M. end Filpula, D. 1991. Single-chain Fv proteins and their fusion proteins. Methods: A comparison to methods in Enzymology. Vol. 2 pp 1–9.

Throughout this application, various publications have been referenced. The disclosures in these publications are incorporated herein by reference in order to more fully describe the state of the art.

The invention being thus described, it will be obvious that the same may be varied in many ways. Such variations are not to be regarded as a departure from the spirit and scope of the invention and all such modifications are intended to be included within the scope of the following claims.

I claim:

1. A plasmid identified in FIG. 2c as pTC4.

2. A plasmid identified in FIG. 2d as pTC5.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 836 base pairs
      (B) TYPE: nucleic acid
      (C) STRANDEDNESS: unknown
      (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
ACTGGAGGCT GATTTTTGAA GAAAGGGGTT GTAGCCTAAA AGATGATGGT GTTAAGTCTT      60
CTGTACCTGT TGACAGCCCT TCCGGGTATC CTGTCAGAGG TGCAGCTTCA GGAGTCAGGA     120
CCTAGCCTCG TGAAACCTTC TCTGACTCTG TCCCTCACCT GTTCTGTCAC TGGCGACTCC     180
ATCACCAGTG GTTACTGGAA CTGGATCCGG AAATTCCCAG GGAATAAACT TGAGTACATG     240
GGGTACATAA GCTACAGTGG TAGCACTTAC TACAATCCAT CTCTCAAAAG TCGAATCTCC     300
ATCACTCGAG ACACATCCAA GAACCAGTAC TACCTGCAGT TGAATTCTGT GACTACTGAG     360
GACACAGCCA CATATTACTG TGCAAGATAT GGTGGTAACT ATGCTATGGA GTACTGGGGT     420
CAAGGAACCT CAGTCACCGT CTCCTCAGGA GGTGGCGGTA CAGGTGGCGG AGGTACAGGC     480
GGAGGTGGTA GAATTGTGAT GACACAGTCT CCATCCTCCC TGGCTATGTC AGTAGGACAG     540
AAGGTCACTA TGAGCTGCAA GTCCAGTCAG AGCCTTTTAA ATAGTAGCAA TCAAAAGAAC     600
TATTTGGCCT GGTACCAGCA GAAACCAGGA CAGTCTCCTA AACTTCTGGT ATACTTTGCA     660
TCCACTAGGG AATCTGGGGT CCCTGATCGC TTCATAGGCA GTGGATCTGG GACAGATTTC     720
ACTCTTACCA TCAGCAGTGT GCAGGCTGAA GACCTGGCAG ATTACTTCTG TCAGCAACAT     780
TATAGCACTC CGTGGACGTT CGGTGGAGGC ACCAAGCTGG AAATCAAACG GGCTGA        836
```